(12) United States Patent
Morisaki et al.

(10) Patent No.: US 7,265,064 B2
(45) Date of Patent: Sep. 4, 2007

(54) SEMICONDUCTOR DEVICE WITH POROUS INTERLAYER INSULATING FILM

(75) Inventors: Hiroshi Morisaki, Tsurugashima (JP); Shinji Nozaki, Kawasaki (JP)

(73) Assignee: Semiconductor Technology Academic Research Center, Tokyo (JP)

( * ) Notice: Subject to any disclaimer, the term of this patent is extended or adjusted under 35 U.S.C. 154(b) by 58 days.

(21) Appl. No.: 10/938,107

(22) Filed: Sep. 10, 2004

(65) Prior Publication Data

US 2005/0032256 A1 Feb. 10, 2005

Related U.S. Application Data

(62) Division of application No. 10/131,949, filed on Apr. 24, 2002, now Pat. No. 6,812,163, which is a division of application No. 09/280,868, filed on Mar. 29, 1999, now Pat. No. 6,566,756.

(30) Foreign Application Priority Data

Mar. 31, 1998 (JP) .................................. 10-103967

(51) Int. Cl.
*H01L 21/31* (2006.01)
(52) U.S. Cl. ........................ 438/787; 438/960; 438/622
(58) Field of Classification Search ................ 438/623, 438/787, 960, 409, 622
See application file for complete search history.

(56) References Cited

U.S. PATENT DOCUMENTS

| 5,103,288 A | 4/1992 | Sakamoto et al. |
| 5,461,003 A | 10/1995 | Havemmann et al. |
| 5,468,685 A | 11/1995 | Orisaka et al. |
| 5,470,801 A | 11/1995 | Kapoor et al. |
| 5,470,802 A | 11/1995 | Gnade et al. |
| 5,472,913 A | 12/1995 | Havemmann et al. |
| 5,494,859 A | 2/1996 | Kapoor |
| 5,693,557 A * | 12/1997 | Hirao et al. ................ 438/398 |
| 5,789,819 A | 8/1998 | Gnade et al. |
| 5,804,454 A | 9/1998 | Mori et al. |
| 5,830,532 A * | 11/1998 | Tang et al. ............ 427/255.18 |
| 5,965,202 A | 10/1999 | Taylor-Smith et al. |

(Continued)

FOREIGN PATENT DOCUMENTS

JP 1-235254 9/1989

(Continued)

OTHER PUBLICATIONS

Wolf et al., Silicon Processing for the VLSI Era, vol. 1-Process Technology; Sunset Beach, CA: Lattice Press, 1986, pp. 230-234.*

(Continued)

*Primary Examiner*—M. Wilczewski
(74) *Attorney, Agent, or Firm*—Christensen O'Connor Johnson Kindness PLLC

(57) ABSTRACT

In a method of manufacturing a semiconductor device, semiconductor circuit elements or wiring patterns are formed on a semiconductor substrate then, a porous semiconductor oxide film is formed as an interlayer insulating film on the semiconductor substrate including the semiconductor circuit elements or wiring patterns by oxidizing semiconductor substance in a mixture gas containing an oxygen gas in a chamber.

12 Claims, 13 Drawing Sheets

U.S. PATENT DOCUMENTS

| | | | |
|---|---|---|---|
| 6,066,573 A | 5/2000 | Muroyama | |
| 6,171,945 B1 * | 1/2001 | Mandal et al. | 438/622 |
| 6,180,507 B1 * | 1/2001 | Lan | 438/618 |
| 6,246,105 B1 * | 6/2001 | Morozumi et al. | 257/640 |
| 6,255,156 B1 * | 7/2001 | Forbes et al. | 438/235 |
| 6,404,025 B1 * | 6/2002 | Hshieh et al. | 257/409 |
| 6,566,756 B1 * | 5/2003 | Morisaki et al. | 257/758 |
| 6,812,163 B2 * | 11/2004 | Morisaki et al. | 438/787 |

FOREIGN PATENT DOCUMENTS

| | | |
|---|---|---|
| JP | 4-116155 | 4/1992 |
| JP | 6-232117 | 8/1994 |
| JP | 7-335880 | 12/1995 |
| JP | 8-83839 | 3/1996 |
| JP | 8-162450 | 6/1996 |
| KR | 96-9050 | 3/1999 |

OTHER PUBLICATIONS

Translation of Office Action for U.S. Appl. No. 10-103967, Japanese Patent Office.

* cited by examiner

DEPOSITION OF SUPER-FINE PARTICLE FILM
ON 1-μm LINE

DEPOSITION OF SUPER-FINE PARTICLE FILM
ON 1-μm LINE

DEPOSITION OF SUPER-FINE PARTICLE FILM
ON 0.5-μm LINE

DEPOSITION OF SUPER-FINE PARTICLE FILM
ON 0.25-μm LINE

SEMICONDUCTOR DEVICE WITH POROUS INTERLAYER INSULATING FILM

CROSS-REFERENCE TO RELATED APPLICATIONS

This application is a divisional of prior application Ser. No. 10/131,949, filed Apr. 24, 2002 now U.S. Pat. No. 6,812,163, which is a divisional of prior application Ser. No. 09/280,868, filed Mar. 29, 1999 now U.S. Pat. No. 6,566,756, priority from the filing date of which is hereby claimed under 35 U.S.C. §120.

BACKGROUND OF THE INVENTION

1. Field of the Invention

The present invention relates to a semiconductor device and a method of manufacturing the same. More particularly, the present invention relates to a semiconductor device using a porous semiconductor oxide film as an interlayer insulating film and a method of manufacturing the same.

2. Description of the Related Art

Recently, a design rule has been shortened to 0.25 μm or less in a semiconductor device such as a micro processor. For this reason, severe problems occur in a process of manufacturing the semiconductor device having such a finer design rule. The problems cannot be solved by a conventional manufacturing technique. For example, one of the problems is a delay due to R×C, where R is a wiring resistance and C is a wiring capacitance. This problem becomes an obstacle to an improvement in a LSI performance based on a high speed operation of transistors. Unless any counter-plan is carried out, the Moore's law can not be maintained.

A technique to increase an operational frequency of an LSI is clear in the manufacturing process of an LSI having 0.25-μm design rule. It is enough to miniaturize the transistor and then shorten the length of a gate. Thus, a switching speed of the transistor can be increased. However, recently, this method cannot be applied any longer. Increase of the switching speed of the transistor contributes only a little to the improvement of the operation speed of the LSI. This is because most of processors have critical paths through which signals are transmitted from an end of the LSI to another end thereof. Thus, the delay due to the time constant RC in a wiring pattern largely contributes to the operation speed of the LSI. Typically, reduction of a design rule makes the operational frequency higher. This is because the maximum length of a signal transmission path becomes shorter. However, when it is intended to produce a new LSI having a size larger than that of the conventional LSI by a new manufacturing process, it becomes difficult to improve the operational frequency of the new LSI.

The metal wiring patterns in such an LSI are roughly classified into a very fine wiring pattern group, a slightly thick wiring pattern group and a bus line. The very fine wiring pattern group is referred to as local wiring patterns through which a data within a function block is transmitted. The slightly thick wiring pattern group is referred to as global wiring patterns, through which a clock signal and power are supplied to the function block. The bus line is used to transmit data between the function blocks. These wiring patterns are generally formed on an insulating layers referred to as an interlayer insulating film.

Now, a width and thickness of the local wiring pattern used for the most advanced LSI having the design rule of 0.18 μm is approximately 0.2 μm. Such local wiring patterns are laid in the same interval of 0.2 μm. On the other hand, the global wiring pattern has various widths from 5 to 100 μm. Multi-layer metal wiring patterns are electrically connected through metals such as tungsten (W) embedded in fine holes referred to as a via hole or a through hole and formed in an interlayer insulating film.

These metal wiring patterns are further made finer for an LSI with the design rule of 0.1 μm. A problem in making the multi-layer wiring pattern fine is the increase of the RC delay due to increase of the wiring resistance of a global wiring pattern. The wiring resistance increases with increase of the chip size of the LSI, and an inter-pattern capacitance increases due to the reduction of a gap between the local wiring patterns.

As a method of reducing the wiring pattern resistance R, it is enough to select a wiring pattern material having a smaller resistivity. For example, it is considered to use Cu or Au instead of Al that has been used up to now, and it is actually used in a partial field. Although Cu is a material having a very small resistance so that Cu is effective in reducing the wiring pattern resistance, it is easy to be diffused into Si. Thus, a barrier layer is needed on the surface of a silicon film. Although Au has a small resistance, it requires the barrier layer similarly to Cu. Therefore, Au does not have an advantage over Cu.

Reduction of the wiring pattern capacitance C is possible by replacing a $SiO_2$ film with a low dielectric material such as a fluorine doped $SiO_2$ or an organic insulating film. The fluorine doped $SiO_2$ film has a dielectric constant lower than that of $SiO_2$. However, the fluorine doped $SiO_2$ film would be still high in a dielectric constant in future. Also, the organic insulating film lacks in the stableness at a high temperature and the wiring pattern material diffuses into the organic insulating film. Although the most excellent dielectric substance is vacuum, it is the atmosphere in view of the practical use. The relative dielectric constant thereof is substantially equal to "1".

The technique referred to as an air bridge is known in which all the dielectric films are removed to float a wiring pattern in the space. However, it requires a number of poles such that a resonance frequency of the wiring pattern extremely exceeds a signal frequency used in the chip so as to support and protect the wiring pattern and protect against destruction resulting from a vibration. Although this method is already successful, it results in a high manufacturing cost. Therefore, it will be a long time before this method is actually used.

The reason of the increase of RC product due to the change of the design rule will be described below. Although an actual LSI has the five to six wiring pattern layers, the case of the two layers will be considered below in order to simplify the analysis.

The important dimension in the wiring pattern is a wiring pattern pitch, which determines the shortest distance between the wiring patterns and the minimum size of the chip. A usual wiring pattern pitch is approximately two times the width of the wiring pattern. The change from the manufacturing process for a 0.5-μm wiring pattern to that for a 0.25-μm wiring pattern reduces the wiring pattern width W to a half. Since an area of the chip is proportional to the square of W at this time, the area of the chip is reduced to the quarter.

On the other hand, the resistance of the metal wiring pattern is inversely proportional to a sectional area (TW). The increase of the resistance leads to the main cause of the delay. Unavoidably, the resistance must be reduced by maintaining the thickness T of a metal pattern or making it thicker. However, the increase of the film thickness of the wiring pattern increases a capacitance between the wiring patterns in a horizontal direction. This is because an area of portions opposite to and parallel to each other is increased irrespective of the reduction of the width between the metal wiring patterns.

As mentioned above, the increase of the capacitance and the increase of the resistance are in the relation of trade-off. Therefore, the approach of suppression of the RC product from the wiring pattern design reaches its limit.

Now, the material used for an interlayer insulating film is $SiO_2$, and the relative dielectric constant thereof is approximately 4.0. This value is still high. Thus, it is said that $SiO_2$ could be used until the present generation of 0.25 µm at the most. Therefore, various materials other than fluorine doped $SiO_2$ are studied to reduce the dielectric constant.

SiOF has a merit that the conventional process can be substantially directly used, and is put to a practical use in a partial field. It can be manufactured by using a PE-CVD (Plasma Enhanced Chemical Vapor Deposition) method, similarly to $SiO_2$. As a material gas, $C_2F_6$ is used in addition to the $SiO_2$ material gas such as TEOS (Tetraethoxysilane; $Si(OC_2H_5)_4$). It is reported that a vast addition of the fluorine reduces an $\in$ value to about 2.7. However, the moisture absorption is increased in conjunction with the increase of F element amount. This results in the increase of the dielectric constant. The practical value is in a range 3.2 to 3.4, resulting in the insufficient effect of the $\in$ reduction. Moreover, it is necessary to protect the wiring pattern against corrosion due to free fluorine.

The smaller dielectric constant of an interlayer insulating film using SOG (Spin on Glass) is rapidly vigorously studied in recent years. The most commonly studied material is an inorganic system hydrogen containing SOG (Hydrogen Silsesquioxane; HSQ). Its chemical formula is $(HSiO_{1.5})_{2n}$ (n equal to 3 to 8). After a coating process, a strong shrinkage stress is brought about when a heat treatment is performed. If the hydrogen containing SOG film is filled between the wiring patterns, the shrinkage stress can not be released. Accordingly, it becomes porous. Thus, the dielectric constant in the horizontal direction is considered to be especially reduced. Therefore, the dielectric constant is 2.2 in the horizontal direction and 2.7 in the vertical direction. Since there is also an example suitable for a mass production, the anxiety of reliability is considered to be little. However, ① the shrinkage stress causes a crack to be brought about, ② the heat-proof temperature is lower than 400° C., and ③ the heat treatment must be performed in ambience with no oxygen because of the hydrogen containing. Therefore, the process must be strictly managed because of the above mentioned reasons.

In the above-mentioned air bridge method, a dielectric material portion is removed so as to float a wiring pattern in the space. The atmosphere basically exists between the wiring patterns. The relative dielectric constant is substantially "1". Now, it is barely used in a high speed bipolar type circuit.

Actually, the long distance air bridge must be supported by posts. The weight of the wiring patterns can be supported without the poles. However, if the distance between the wiring patterns is short, the influence of electromagnet force becomes strong so that a wiring pattern having no pole may be bent. Moreover, there is a problem of a resonance frequency. If electric signals transmitted on the wiring patterns adjacent to each other are oscillated at the resonance frequency, the wiring pattern is broken. For this reason, it is necessary that the poles are provided at an adequate interval so that the resonance frequency is extremely higher than the signal frequency of the chip. Thus, although the capacitance is slightly increased by the posts, the entire dielectric constant is merely larger by 10 to 20% than the atmosphere.

On the other hand, a problem in the air bridge method is in complication of the process. It is necessary to remove by etching, the dielectric layer while leaving the portion of the posts. Another problem is that the air bridge must be sealed. This may be not used for a long time because of the increase in cost. However, this is the most attractive in decreasing the dielectric constant.

As mentioned above, a new material for the interlayer insulating film is required to have the properties listed below:

a small dielectric constant;
an adaptation to a wiring pattern material;
a heat-proof property; and
an adaptation to a process.

The large reduction of the dielectric constant cannot be expected in the method of doping fluorine elements on a silicon oxide film. Therefore, it is expected to reduce the dielectric constant by decreasing a density. Also, the small dielectric constant is expected in the organic material. As for the adaptation to the wiring pattern material, metal ions are easy to be doped by electro-migration in a case of the organic material so that the insulating film is damaged. As for the heat-proof property, the glass transition temperature of the interlayer insulating film must be equal to or higher than 400° C. in relation to the process. Softening of the interlayer insulating film and increase of a thermal expansion coefficient of insulating film material are brought about by heating the insulating film. The temperature at this time is the glass transition temperature. If a process temperature exceeds the glass transition temperature, the wiring pattern is largely deformed and destroyed. Thus, the stability at the high temperature is required to the interlayer insulating film. In this point, the silicon oxide film is superior to other material films. As for the adaptation to the process, the practical use is difficult unless the cost performance is excellent, in view of the adaptation to other manufacturing processes.

SUMMARY OF THE INVENTION

The present invention is accomplished in view of the above mentioned problems. Therefore, an object of the present invention is to provide a semiconductor device including an interlayer insulating film with a small dielectric constant.

Another object of the present invention is to provide a semiconductor device including an interlayer insulating film with a heat-proof property.

Still another object of the present invention is to provide a semiconductor device including an interlayer insulating with an adaptability to a currently used process.

It is also an object of the present invention to provide a method of manufacturing the above semiconductor devices.

In order to achieve an aspect of the present invention, a method of manufacturing a semiconductor device, includes the steps of:

forming semiconductor circuit elements or wiring patterns on a semiconductor substrate;

forming a porous semiconductor oxide film as an interlayer insulating film on the semiconductor substrate including the semiconductor circuit elements or wiring patterns by oxidizing semiconductor substance in a mixture gas containing an oxygen gas in a chamber.

The porous semiconductor oxide film is a porous silicon oxide film.

The step of forming a porous semiconductor oxide film includes:

supplying-the mixture gas containing the oxygen gas into the chamber; and vaporizing silicon as the semiconductor substance in the chamber.

In this case, the pressure of the mixture gas in the chamber is preferably in a range 0.3 Torr to 10 Torr, and more preferably in a range 0.5 Torr to 10 Torr.

The pressure of the mixture gas in the chamber may be set to a predetermined value, or be changed while the mixture gas is supplied. At this time, the pressure of the mixture gas may be set to a first predetermined value and then to a second predetermined value larger than the first predetermined value. Further, the pressure of the mixture gas may be set to a third predetermined value small than the second predetermined value after being set to the second predetermined value.

Also, the mixture gas containing the oxygen gas into the chamber may be supplied such that the porous silicon oxide film covers the semiconductor circuit elements or wiring patterns while filling between the semiconductor circuit elements or wiring patterns. Instead, the mixture gas containing the oxygen gas into the chamber may be supplied such that the porous silicon oxide film covers the semiconductor circuit elements or wiring patterns while forming air portions on side walls of the semiconductor circuit elements or wiring patterns.

The aspect ratio of a space between the semiconductor circuit elements or wiring patterns is preferably equal to or smaller than 1.6, more preferably equal to or smaller than 0.8.

It is desirable that the mixture gas includes an inert gas and the oxygen gas, and contains the oxygen gas substantially equal to 1%.

Also, it is desirable that the porous semiconductor oxide film includes holes of an average diameter equal to or less than 20 nm, and includes $SiO_2$ equal to or more than 85%. In addition, the porous silicon oxide film is formed to have a relative dielectric constant equal to or smaller than 1.95.

In order to achieve another aspect of the present invention, a method of manufacturing a semiconductor device, includes the steps of:

forming semiconductor circuit elements or wiring patterns on a semiconductor substrate;

supplying a mixture gas containing an oxygen gas into a chamber;

vaporizing silicon in the chamber to produce silicon oxide particles; and forming a porous silicon oxide film as an interlayer insulating film on the semiconductor substrate including the semiconductor circuit elements or wiring patterns from the silicon oxide particles in a chamber.

In order to achieve still another aspect of the present invention, a semiconductor device includes semiconductor circuit elements or wiring patterns formed on a semiconductor substrate, and a porous silicon oxide film formed as an interlayer insulating film on the semiconductor substrate including the semiconductor circuit elements or wiring patterns. The porous silicon oxide film includes holes of an average diameter equal to or less than 20 nm.

The porous silicon oxide film may cover the semiconductor circuit elements or wiring patterns while filling between the semiconductor circuit elements or wiring patterns. Instead, the porous silicon oxide film may cover the semiconductor circuit elements or wiring patterns while forming gaps on side walls of the semiconductor circuit elements or wiring patterns.

In this case, an aspect ratio of a space between said semiconductor circuit elements or wiring patterns is equal to or smaller than 1.6, and the porous silicon oxide film includes $SiO_2$ equal to or more than 85% to have a relative dielectric constant equal to or smaller than 1.95.

DESCRIPTION OF THE PREFERRED EMBODIMENTS

Figure 1A:
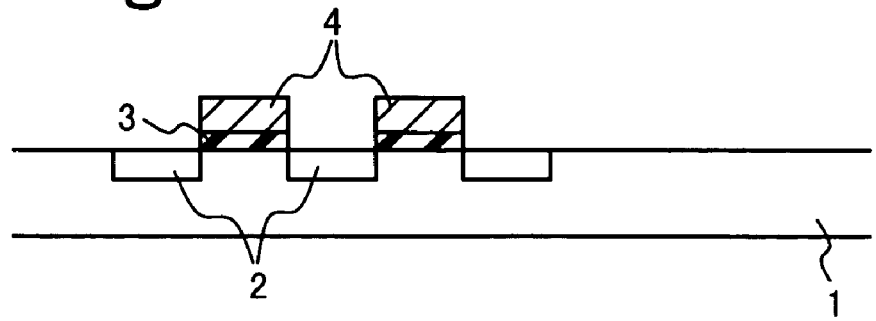
FIGS. 1A and 1B are cross section views explaining a method of manufacturing a semiconductor device of the present invention.

The semiconductor device of the present invention will be described below with reference to the attached drawings.

A gas evaporation method is a method of heating and vaporizing substance for fine particles and cooling the vapor thereof and then condensing into super-fine particles. This method is usually performed in an inert gas. The vapor produced by the vaporizing process is diffused in the gas and gradually cooled and becomes in a supersaturated state so that nucleation is performed. A vapor expanding region is formed on the vaporization surface as a vapor region. The nucleation is performed outside the vapor expanding region. A most portion of the vapor is condensed substantially simultaneously into super-fine particles (vapor growth). These particles are carried and raised through convection. The vapor is cooled in conjunction with the rise, and then, the vapor growth is stopped. However, the particles are collided against each other and fused (fuse growth). After that, they are deposited on a substrate.

A super-fine particle silicon oxide ($SiO_x$) film formed by the gas evaporation method has the structure and the characteristics described below. That is, the film is a thin film composed of the super-fine particles and the ambient gas. Thus, the dielectric constant thereof is expected to be small. Metal ions have difficulty in passing through the silicon oxide film. Therefore, there is no anxiety of the deterioration of insulation. The silicon oxide film is stable at a high temperature. Since the silicon oxide film is formed by the gas evaporation method, the number of processes is substantially equal to those of the conventional process. Thus, it is superior in cost performance. However, it has an anxiety about moisture absorption because of the porosity. It has an anxiety about the embedding performance because the directionality when the film is formed is low. Thus, if the problems of the moisture absorption and the embedding performance can be solved, the gas evaporation method is especially desirable as a method of manufacturing the interlayer insulating film.

<Electric Conduction in Fine Particle Collection System>

Since the present invention discusses the electric conduction in the entire fine particle film, the conduction is considered with regard to a model of a assembly of fine particles. Many particles are aligned through contact points. A surface adsorption layer (in many cases, water in the atmosphere) exists in the whole thereof. Current running through the particle system is composed of a current component running through the particle itself and the contact point and a current component running through the surface adsorption layer in parallel to the above mentioned route. That is, a specific resistance Rs of the particle and a contact resistance Rc are connected in series, and a resistance R1 of the surface adsorption layer is connected in parallel to them. The entire resistance R in this circuit is calculated by the equation:

$$1/R = 1/(Rs+Rc) + 1/R1 \quad (1)$$

(1) In Case of that Rs is Small (a resistivity $\rho s < 1$ $\Omega$cm)

A relationship of R1>Rc>Rs is typically established in a case of a conductive particle. Thus, the equation (1) becomes approximately R≈Rc. Therefore, the entire resistance R is approximately determined by the contact resistance.

(2) In Case of that Rs is Approximately Middle (1 $\Omega$cm < $\rho s$ < $10^8$ $\Omega$cm)

Rc is relatively small in a case of a semiconductor particle if it is in a densely filled state. Thus, a relationship of R1>Rs>Rc is established. Then, the equation (1) becomes approximately R≈Rc. However, when Rs is approximately middle, the relationship of magnitude between Rs, Rc and R1 changes in accordance with the situation. Therefore, it is difficult to perform the approximate calculation, in many cases.

(3) In Case of that Rs is Large ($10^8$ $\Omega$cm < $\rho s$)

A relationship of Rs, Rc>R1 is typically established in a case of an insulation particle. Thus, the equation (1) becomes approximately R≈R1. That is, in the case of the insulation particle, the entire resistance R is determined by the resistance R1 on the surface adsorption layer.

<Dielectric Constant of Particle System>

Consider a capacitor in which a dielectric substance having a relative dielectric constant of $\in r$ is filled between two flat plate electrodes parallel to each other. It is supposed that the two flat plate electrodes are S $m^2$ and the distance between the electrodes is d m. The capacitance C is given by:

$$C = \in_r \times \in_o \times S/d$$

where $\in_o$ (=$8.855 \times 10^{-12}$ F/m) is a vacuum dielectric constant.

In the case of the fine particle, the substance does not completely fill the space between the electrodes. A gap is always present. Thus, $\in_r$ implies an apparent relative dielectric constant in which the particles and the air are mixed. Supposing the dielectric constants of the particle and the air to be $\in_1$ and $\in_2$ and volume percentages thereof to be $v_1$ and $v_2$ ($v_1+v_2=1$), consider how the apparent dielectric constant $\in$ in this system is expressed.

In the typical dispersion system of the particles, the particles and the air are mixed in a properly random manner. However, a case in which the particles are distributed only on one side may be considered. In this case, when the two capacitors are connected in series, $\in$ is calculated by the equation:

$$\in^* = 1/(v_1/\in_1 + v_2/\in_2) \quad (2)$$

On the other hand, the two capacitors are connected in parallel, $\in^*$ is calculated by the equation:

$$\in^* = v_1 \in_1 + v_2 \in_2 \quad (3)$$

In the equation (2), $\in^*$ is the smallest. In the equation (3), $\in^*$ is the largest. These equations are referred to as the Wiener's lower limit equation and the Wiener's upper limit equation, respectively. Thus, although the apparatus dielectric constant $\in^*$ has the value between the equations (2) and (3), it is actually impossible to determine the distributed situation. The experiential mixture law is proposed which is expressed as following:

Wiener's general equation, $$1/(\in^* + u) = v_1/(\in_1 + u) + v_2/(\in_2 + u);$$

Lichtencker's logarithmic equation, $$\log \in^* = v_1 \log \in_1 + v_2 \log \in_2; \text{ and}$$

Lichtencker-Rother's power equation, $$\in^* = v_1 \in_1 k + v_2 \in_2 k$$

A porous silicon oxide film used in the present invention will be described below with reference to the drawings. The porous silicon oxide film is manufactured as followings.

Figure 2:
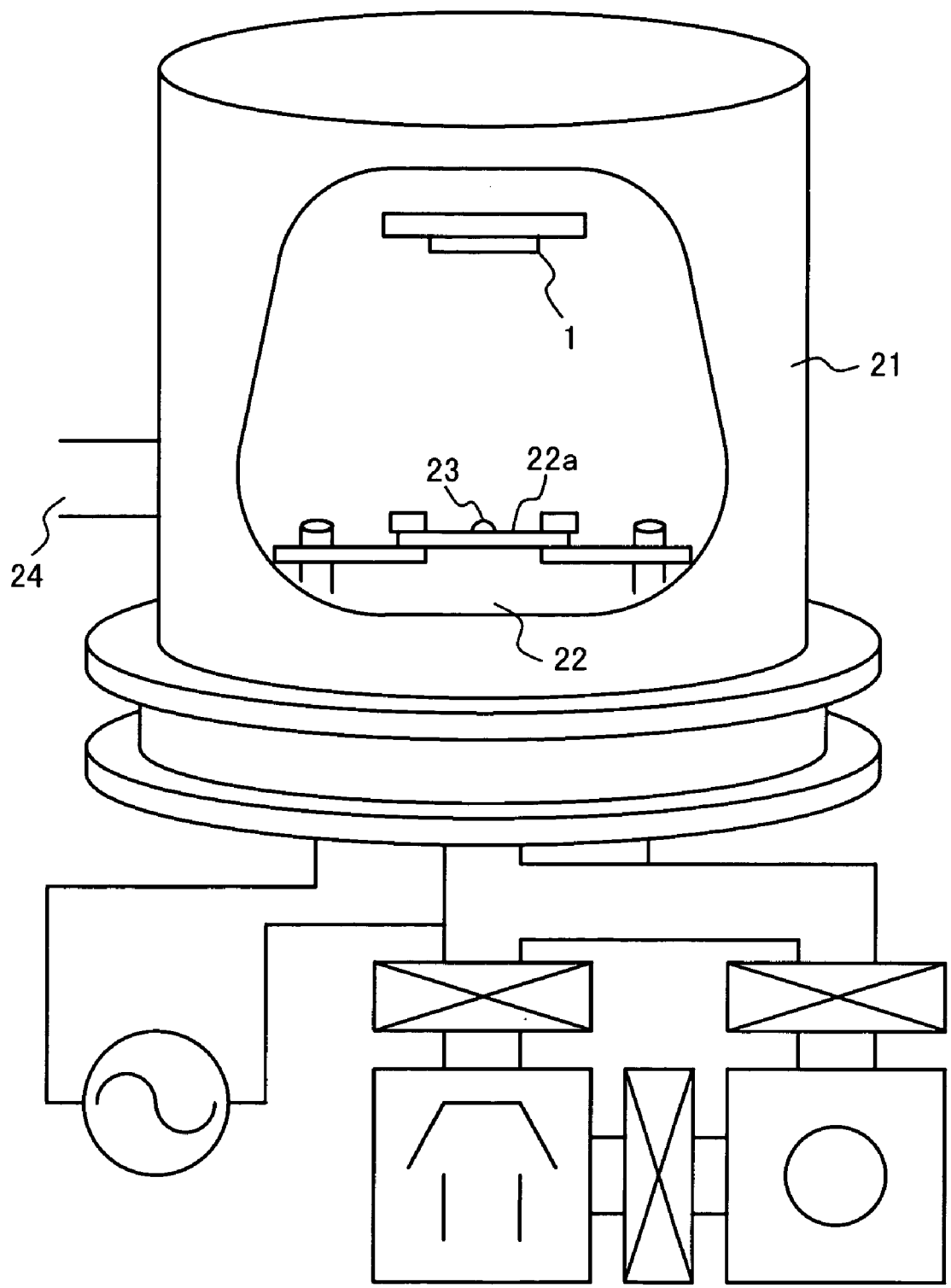
FIG. 2 is a diagram explaining a chamber (sample forming room) used in the method of manufacturing the semiconductor device of the present invention.

As shown in FIG. 2, a silicon substrate 1 is set within a chamber (a production room) 21. After that, a porous semiconductor oxide film 5 is formed.

In the chamber 21, silicon is used for a vapor source 23, and a BN (boron nitride) boat is used for a crucible 22a. As the result of the supply of the electric power to the BN port 22, silicon in the BN boat is heated and vaporized. The mixture gas of $O_2$ and Ar is used for the ambient gas so as to produce the oxidized fine particles. The vaporized silicon collides with the ambient gas and grow as super-fine particles. At the same time, the super-fine particles are oxidized by $O_2$. The oxidized super-fine particles are deposited on the substrate 1 apart by 5 cm from the BN boat 22a to form a porous super-fine particle silicon oxide film. The pressure of the ambient gas is changed between 0.3 Torr and 10 Torr. The growth times are unified into 10 minutes.

The procedure of producing the particles will be described below in detail:

① The inside of the chamber is made to be vacuum until a pressure less than $1.0 \times 10^{-2}$ Torr;

② When the chamber inside is made to be vacuum until a pressure less than $5.0 \times 10^{-6}$ Torr, a vacuum valve is closed. Then, the ambient gas (1% $O_2$ and 99% Ar) is applied until a predetermined pressure;

③ A voltage is applied to the BN boat. While a temperature is measured with a pyrometer, a shutter is opened when the temperature becomes stable. Then, the oxidized super-fine particles are deposited on the substrate. Meanwhile, the periphery of the chamber is cooled by cold water; and ④ After the deposition process is ended, the sample is sufficiently cooled and picked up. Then, this procedure is finished.

At this time, the formed porous silicon oxide film has an average hole diameter described below, on the basis of the pressure of the mixture gas of the oxygen gas and the Ar gas.

The growth process of the particle includes the three stages: (1) the super-saturation stage of the vaporized silicon, (2) the vapor growth and (3) the fusion growth. The large difference from a vacuum vaporization method is in that an average free path of the vaporized silicon is short because of the molecules in the ambient gas. Thus, the particles are generated by the gas evaporation method.

Experimentally, the factors for the diameter of the particle include (a) the temperature of the vaporization source, (b) the distance from the vaporization source to the substrate, (c) the type of the ambient gas and molecular weight and (d) the pressure of the ambient gas.

When the temperature of the vaporization source is increased, and when the molecular weight of the ambient gas is larger, the diameter of the particle becomes larger. Also, when the pressure of the gas is increased, and when the distance from the vaporization source to the substrate is longer, the diameter of the particle becomes larger. However, the particle diameter is saturated at the proper pressure and distance.

There are various conditions in production of the super-fine particles by using the gas evaporation method. The characteristics of the produced super-fine particles are investigated by changing only the pressure of the ambient gas. The investigation starts with the evaluation of the sizes and the shapes of the particles. Then, the conditions to form the porous super-fine particle silicon oxide film are considered by totally examining a dielectric constant, hydrophobic property, leak current and covarage property to the line and the space.

Figure 14:
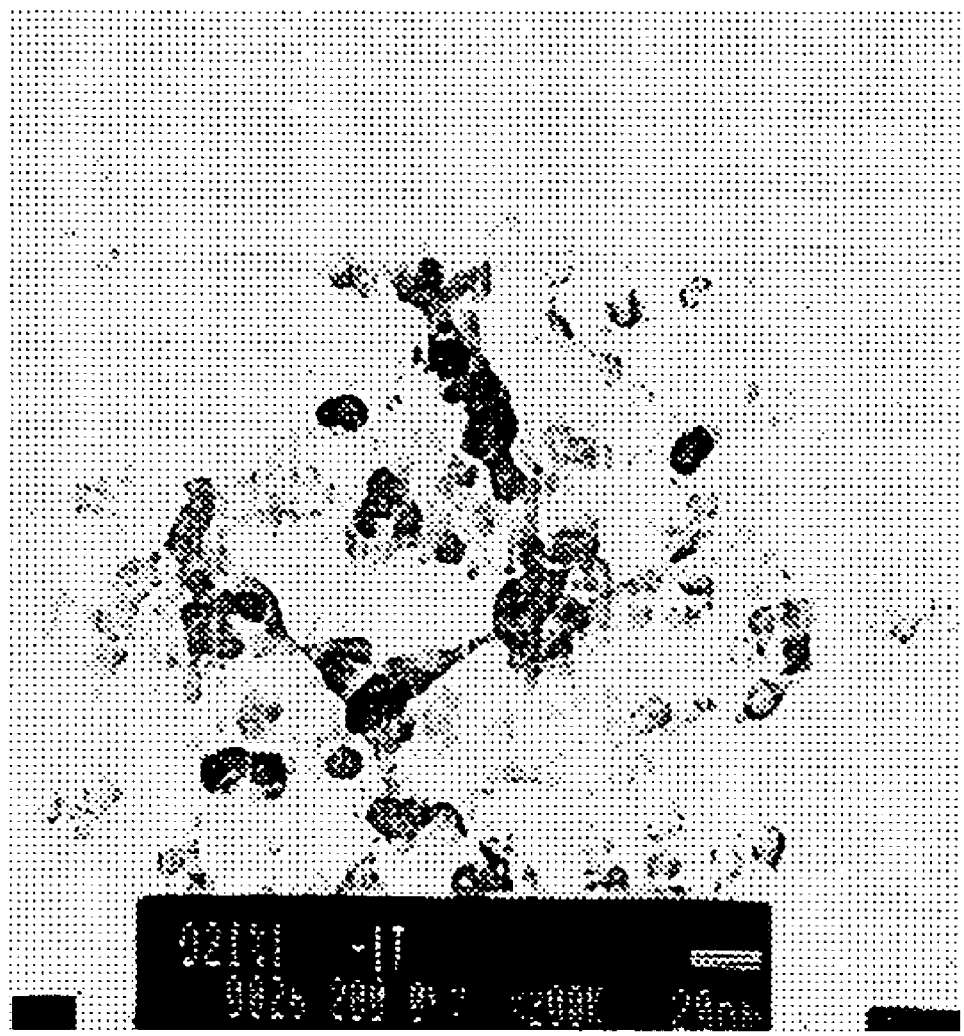
FIG. 14 is a diagram indicating a photograph by a transmission electron microscope of the porous semiconductor oxide film formed at 1 Torr.
Figure 15:
FIG. 15 is a diagram indicating a photograph by a transmission electron microscope of the porous semiconductor oxide film formed at 10 Torr.

At first, it is necessary to confirm the low density that is the condition to attain the low dielectric constant. FIGS. 14 and 15 show TEM images of the super-fine particle films immediately after they are formed at 1 Torr and 10 Torr, respectively. It is typically said that fine particles or super-fine particles in the form of a ball are formed by the gas evaporation method. However, it could be understood from these images that the formed porous silicon oxide film does not have the super-fine particles in the form of the ball.

It can be confirmed that the super-fine particles having diameters of ten-odd nm are coupled to each other in the form of a chain or a network, in the super-fine particle porous silicon oxide film formed at the pressure of 1 Torr. At this time, the average diameter of the formed holes is equal to or less than 20 nm. Also, it is confirmed that a part of the film has the form of the particle, in the porous super-fine particle silicon oxide film formed at the pressure of 10 Torr. However, as a whole, the particles are further fused as compared with the case at the pressure of 1 Torr. As a result, the forms of the particles are collapsed. Thus, although the average diameter of the particles can not be calculated, it surely exceeds 20 nm.

Since there is the gap between the particles which are not coupled, it is considered that the ambient gas in the atmosphere. The size of the particle produced at the pressure of 10 Torr is evidently larger than that of 1 Torr. Moreover, it seems that the gap between the particles produced at the pressure of 10 Torr is wider than that of 1 Torr.

Next various characteristics of the porous silicon oxide film formed at the process similar to the above mentioned process will be described.

Figure 3A:
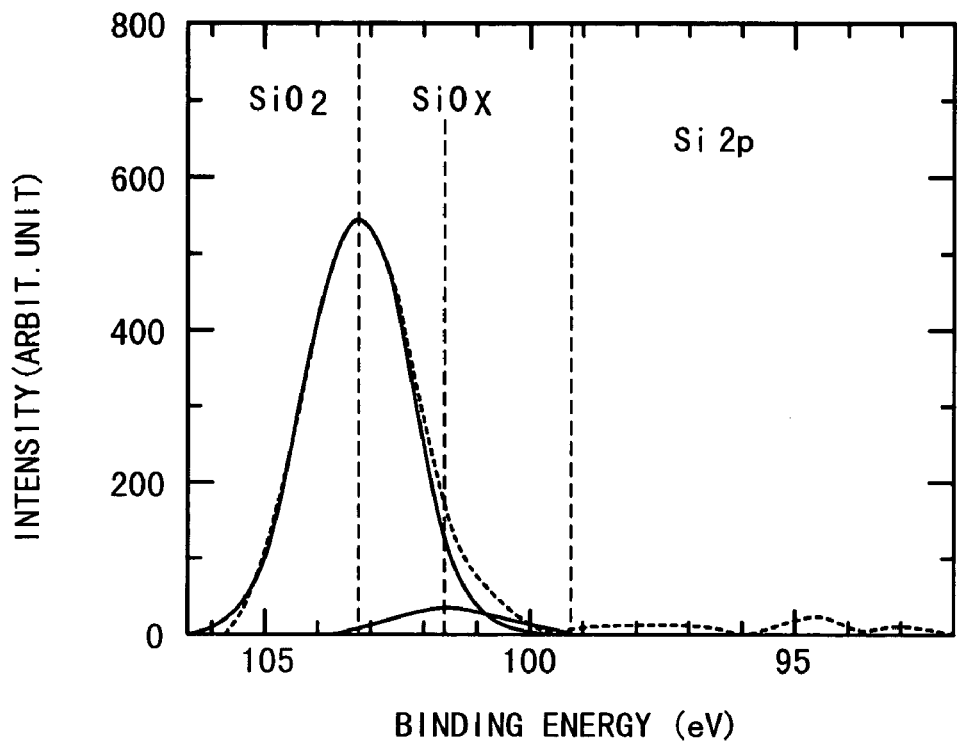
FIGS. 3A and 3B are graphs showing the results of XPS wave separation for porous semiconductor oxide films generated at 1 Torr and 10 Torr, respectively.
Figure 3B:
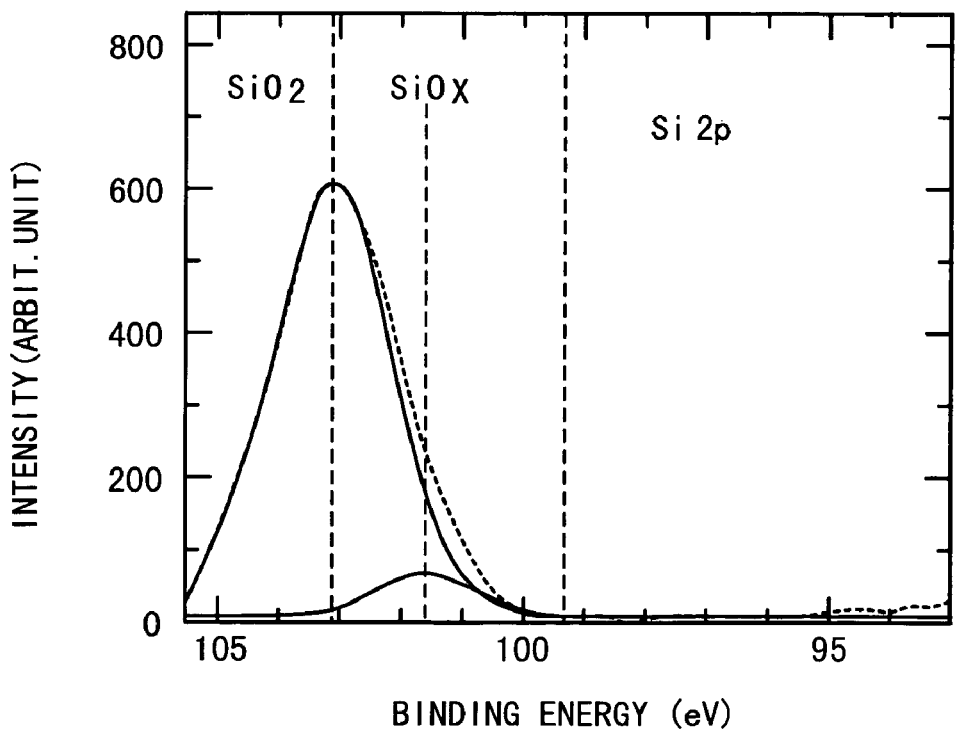

FIGS. 3A and 3B show the result of XPS measurement immediately after the vaporization. $Ar^+$ etching was carried out, and then chemical bond analysis was performed to the particle film. Si and $SiO_2$ are represented by Gaussian distributions with respective peaks as 99.3 eV and 103.3 eV. At first, the measured data is wave-separated into these two distributions, and the surpluses thereof are represented as $SiO_x$. In any case, the $SiO_2$ occupies a greater part than 85%. The integrated intensities of the $SiO_x$ component to the whole are a remaining part.

The device in which the silicon oxide film was sandwiched between flat plate electrodes parallel to each other was used for determination of the dielectric constant. The capacitance of the device was measured by an LCZ meter and then the relative dielectric constant was calculated from the area of the electrode and the thickness of the film.

Figure 4:
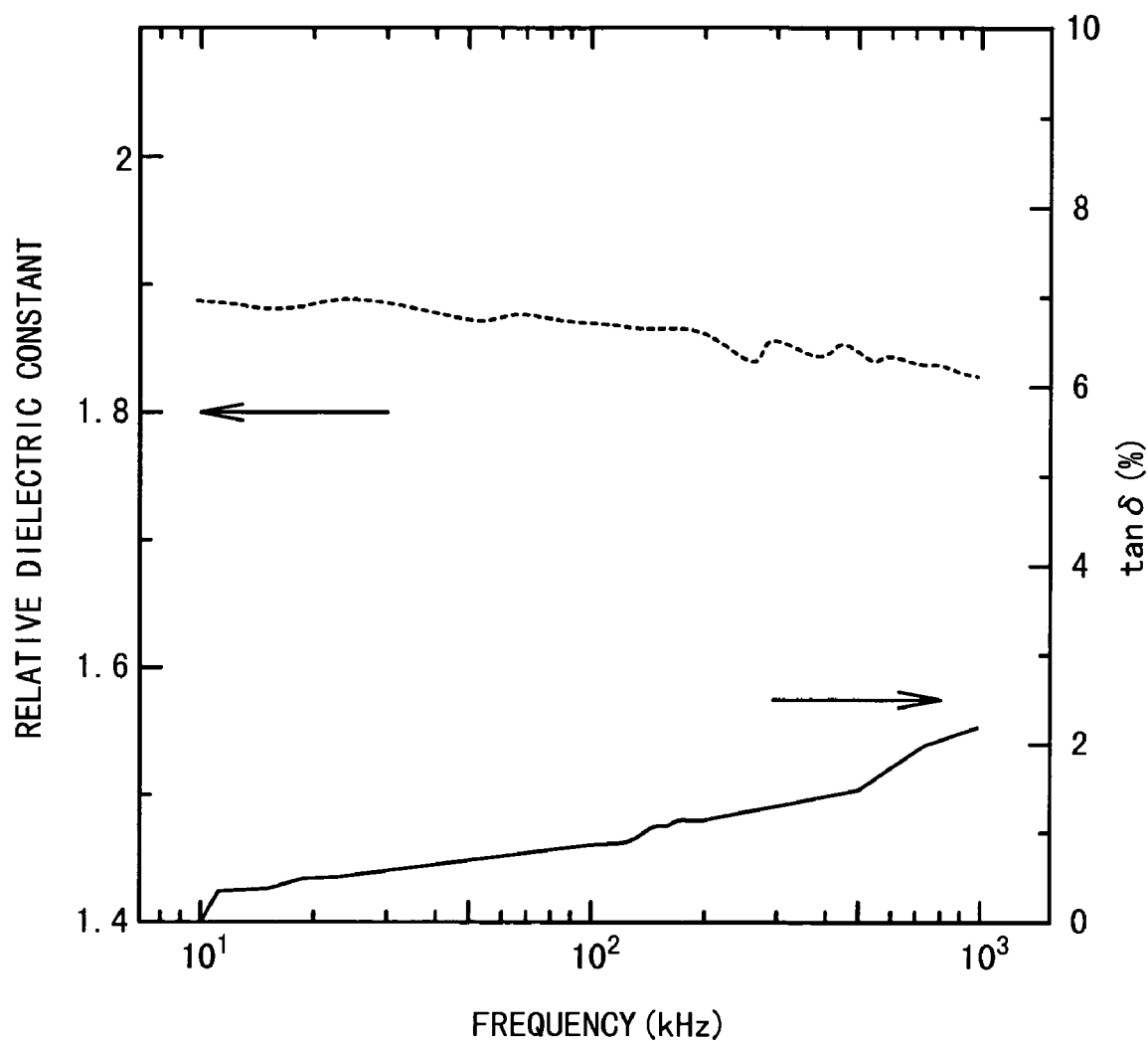
FIG. 4 is a graph showing a dependency on a frequency of a relative dielectric constant of the porous semiconductor oxide film formed at 1 Torr.
Figure 5:
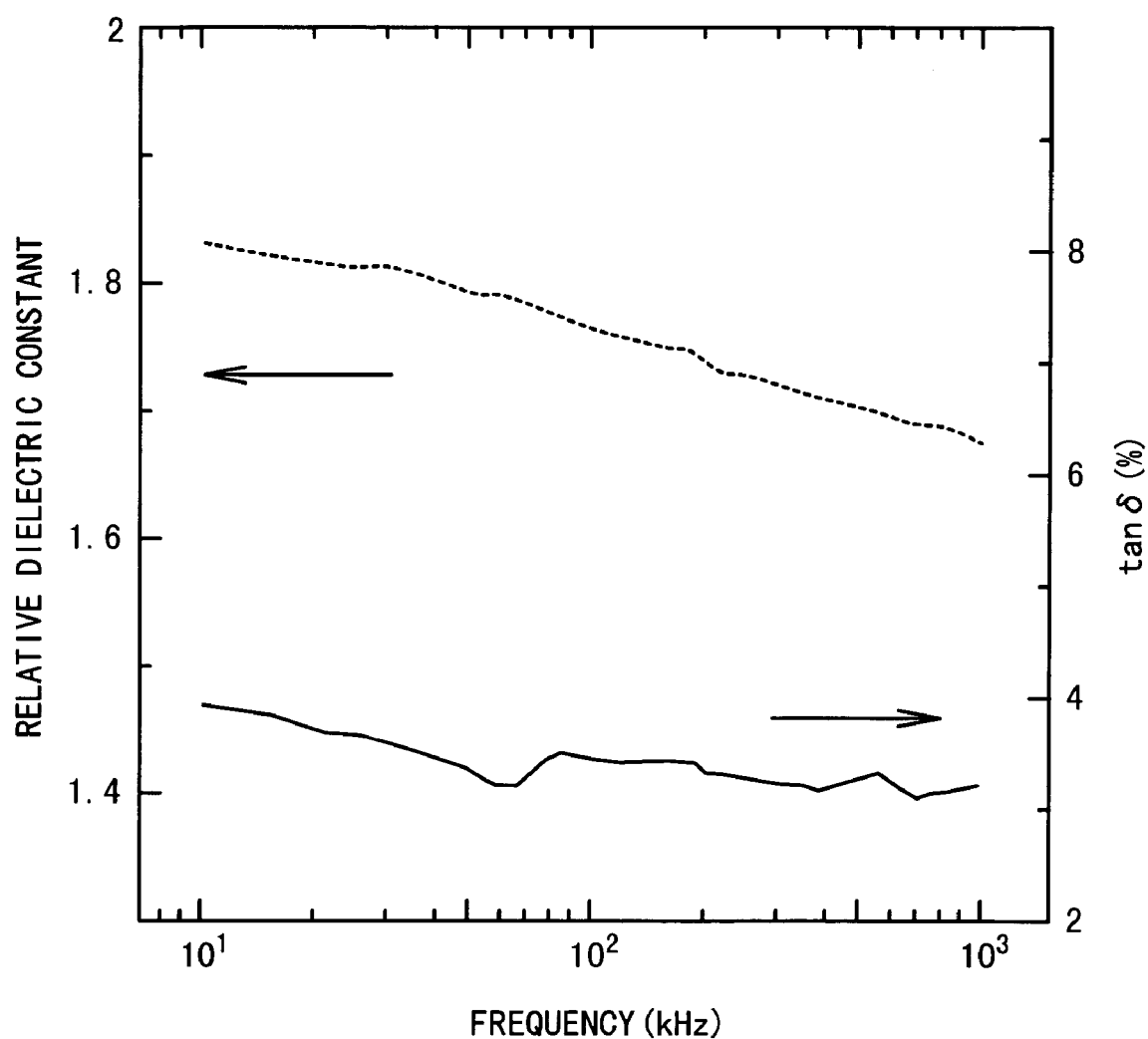
FIG. 5 is a graph showing a dependency on a frequency of a relative dielectric constant of the porous semiconductor oxide film formed at 10 Torr.
Figure 6:
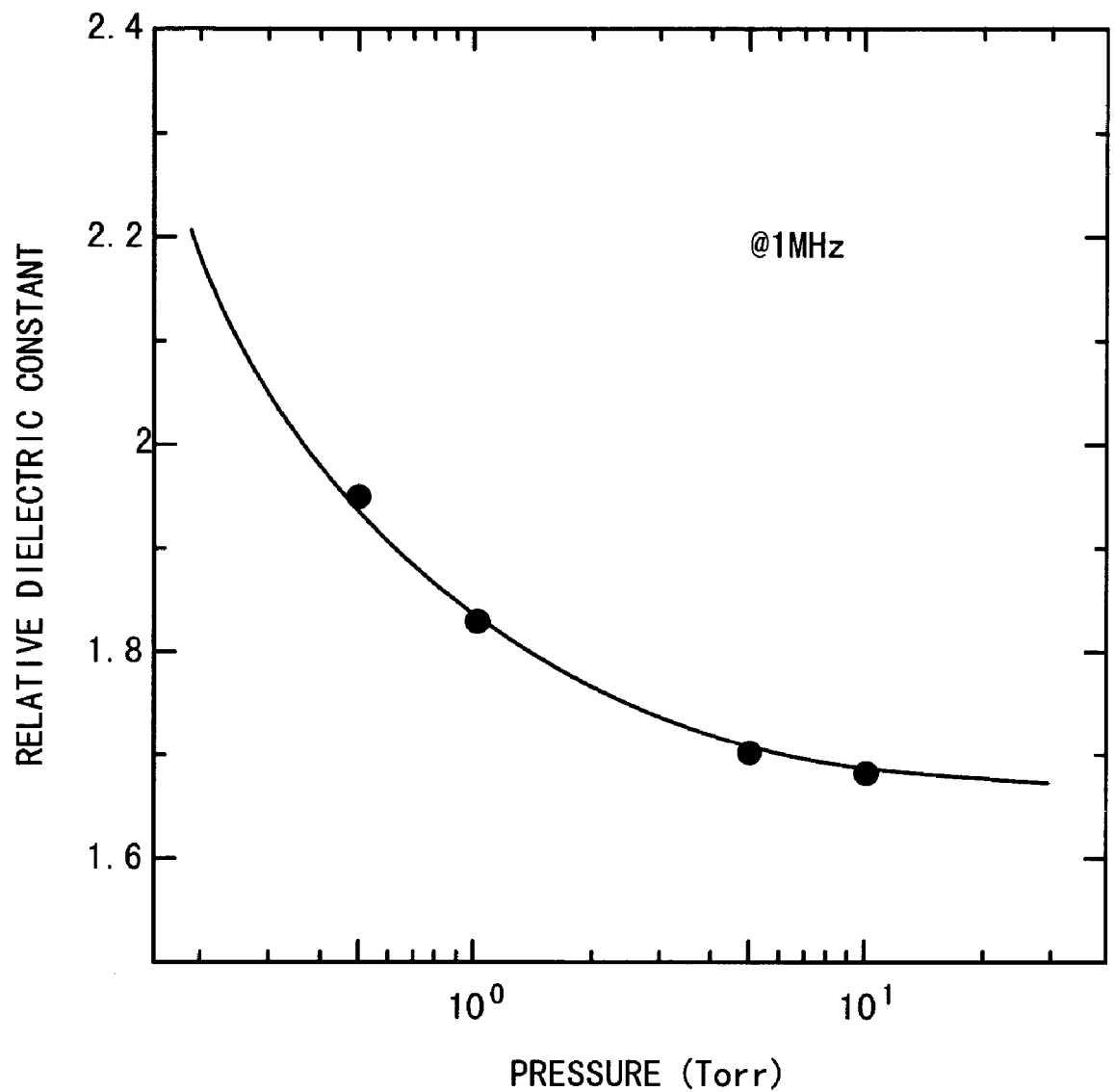
FIG. 6 is a graph showing a dependency of the relative dielectric constant of the porous semiconductor oxide film on a pressure of a mixture gas containing oxygen gas.

FIGS. 4 and 5 show the results of measuring the capacitance and then determining the relative dielectric constant from the approximation of the parallel flat plates. The frequency is plotted on a horizontal axis. The relative dielectric constant is plotted on a left vertical axis, and tan δ is plotted on a right vertical axis. FIG. 6 shows the relative dielectric constant at 1 MHz with respect to the pressure of the ambient gas when the samples are formed as a parameter. In any condition, the relative dielectric constant is extremely reduced as compared with 3.9 of typical $SiO_2$. As for the dependence on the gas pressure, the sample having the smaller dielectric constant is formed, as the pressure is higher. If the degrees of the oxidation are considered to be substantially same, it could be considered that as the sample is formed at the higher pressure, the ratio of a portion occupied by the ambient gas becomes higher in the whole film, because the dielectric constant of the air is substantially "1". The relative dielectric constant at 1 MHz is 1.68 at 10 Torr, 1.70 at 5 Torr, 1.83 at 1 Torr and 1.95 at 0.5 Torr.

The hydrophobic property is evaluated by examining the change of the dielectric constant and the change of the leak current after the formed samples are left in the atmosphere.

Figure 7:
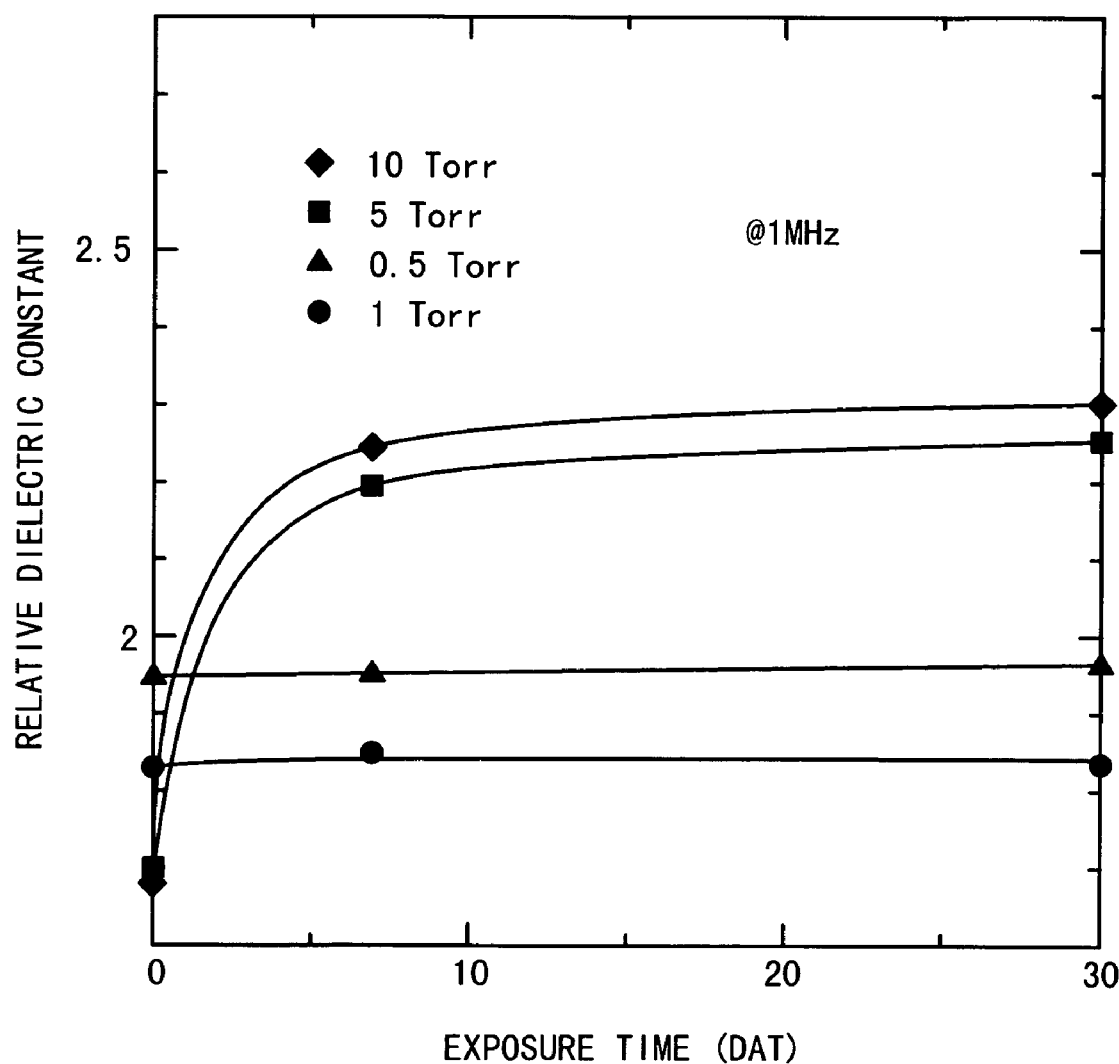
FIG. 7 is a graph showing dependency of the relative dielectric constant of the porous semiconductor oxide films which are formed at various pressures, when it is left in the atmosphere.

The samples were left in the atmosphere so at to measure the deterioration change of the dielectric constant for confirmation of the moisture absorption based on the change of the electric characteristic. FIG. 7 shows the measuring result. Immediately after the film is formed, the sample has the smaller dielectric constant, when the sample is formed under the higher pressure. However, the increase of the dielectric constant is confirmed at 10 Torr and 5 Torr as the time proceeds. On the other hand, any change is not confirmed at 0.5 Torr and 1 Torr even after one month.

The cause of the increase of the dielectric constant is the adsorption of moisture. The relative dielectric constant of the water is approximately "80" at a room temperature. Typically, the structure having the gap such as the super-fine particle film is easy to absorb the moisture in the atmosphere. Thus, it is reasonable to consider that the moisture is absorbed by the samples formed at 10 Torr and 5 Torr. The moisture absorption is not confirmed in the samples formed at 0.5 Torr or 1 Torr. The reasons are considered below. That is, the samples formed at 0.5 Torr and 1 Torr have the large dielectric constant immediately after the formation. Since the ratio of a portion occupied by holes is originally small and the sizes of holes are smaller, it is difficult to absorb the moisture. As shown in the above TEM images, the samples formed at 0.5 Torr or 1 Torr have the film structures which are different from those formed at 10 Torr and 5 Torr and into which the water can not enter. The relative dielectric constant of "1.83" is one of the lowest dielectric constants other than the relative dielectric constant in the air bridge structure, although it is the high dielectric constant as compared with that of the sample formed at 10 Torr.

The insulation property was evaluated by I-V measurement. The same device as the measurement of the capacitance was used. Attention must be paid to the measuring method similarly to that of the capacitance. At first, potentials of a main electrode and a guard electrode are made equal to each other. Then, a voltage was applied between the main electrode and the opposite electrode. It was possible to read only the leak current on the side of the main electrode at this time to thereby measure without influence from a surface current. The leak current was examined for the sample formed at 1 Torr having the smaller dielectric constant among the samples at 0.5 Torr and 1 Torr which had the small dielectric constant film and did not absorb the moisture.

Figure 8:
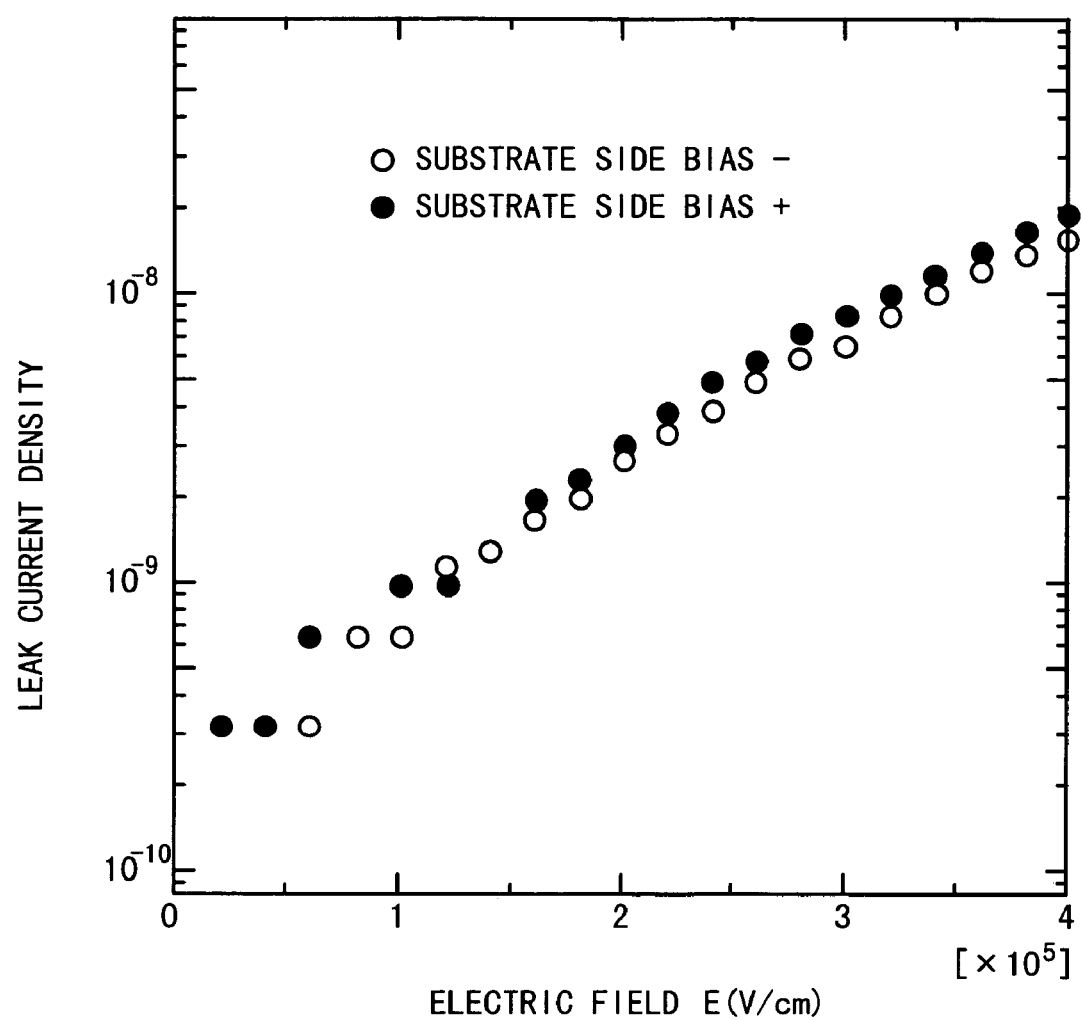
FIG. 8 is a graph showing a relationship between an electric field and a leak current density of the porous semiconductor oxide film generated at the pressure of 1 Torr.
Figure 9:
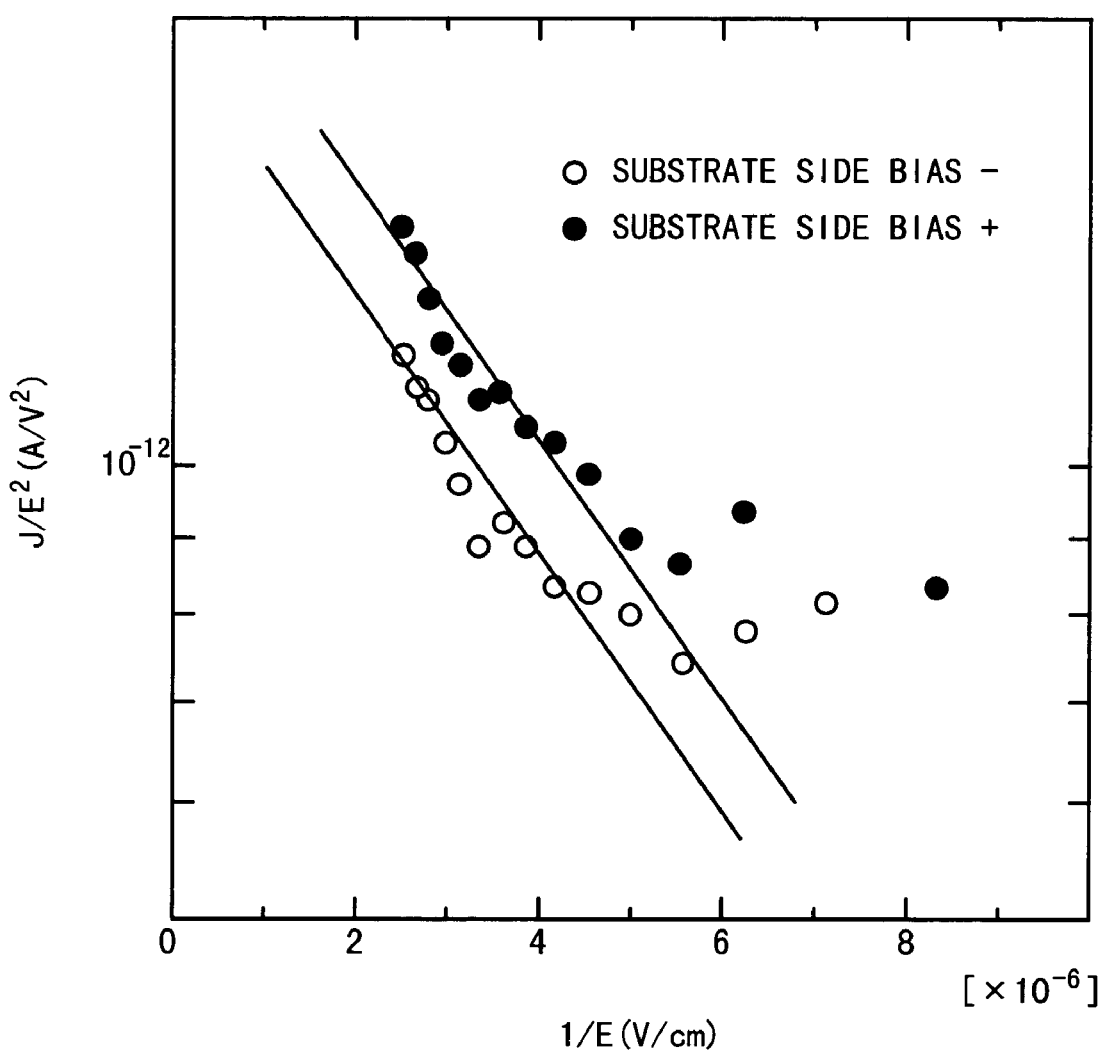
FIG. 9 is a diagram showing a F-N plot of the result shown in FIG. 8.

FIG. 8 shows the result in which the current and the voltage of the super-fine particle film having the film thickness of 500 nm generated at 1 Torr are measured in the practical range of the electric field. In FIG. 8, the electric field is represented on a horizontal axis and the current density is represented on a vertical axis. The super-fine particle film is an excellent insulator because the resistivity calculated from the leak current at $4 \times 10^5$ V/cm is $2.6 \times 10^{13}$ $\Omega$cm FIG. 9 shows the Fowler-Nordheim (hereafter, referred to as F-N) plot into which the result of FIG. 8 is converted. 1/E is indicated on a horizontal axis, and $J/V^2$ is indicated on a vertical axis. The conduction similar to that of the F-N form is indicated under the strong electric field. This conduction is identical to the electric conduction of the $SiO_2$ film in a bulk, and is the tunnel conduction in the strong electric field. At the same time, it can be understood that any trap is not contained in a forbidden band or a small number of traps are contained even if contained.

The slight increase of the leak current is confirmed as compared with that immediately after the formation of the silicon oxide film, as for the change of the leak current when the sample is left in the atmosphere. However, there is no substantial change after seven days and thirty days. Moreover, the increase of the dielectric constant is not confirmed as mentioned above. Therefore, it can be considered that the moisture is not absorbed.

Line patterns of resist were formed by use of electron beam lithography for evaluation of the coating property of the porous silicon oxide film. The line can be considered to be a circuit element or a wiring pattern in the semiconductor integrated circuit. The super-fine particle silicon oxide film is deposited on the resist pattern. The super-fine particle film was deposited at the condition of 1 Torr at which the most excellent electric characteristics as the interlayer insulating film might be realized from the above mentioned results.

Figure 10:
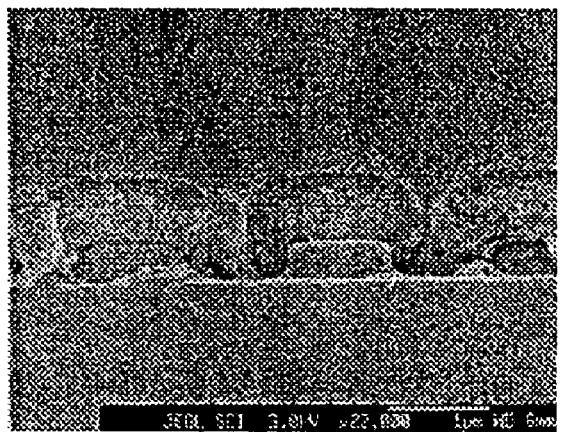
FIG. 10 is a diagram indicating a photograph by an electron microscope which shows a result of deposition of the porous semiconductor oxide film onto lines with a 1 μm pitch.
Figure 11:
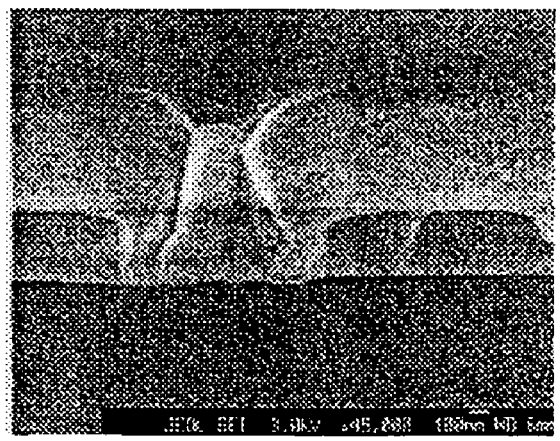
FIG. 11 is a diagram indicating a photograph by the electron microscope which shows a result of deposition of the porous semiconductor oxide film onto lines with a 1 μm pitch.

FIGS. 10 and 11 show sectional SEM images after the super-fine particle film was deposited on 1-µm lines and spaces at the condition of the 1 Torr ambient gas. The super-fine particle silicon oxide film of 0.7 µm was deposited on a resist film thickness of 0.4 µm. An aspect ratio (resist film thickness/space width) was 0.4. In this example, the space between the lines was perfectly filled with the silicon oxide film without any gap.

From the result of the electric characteristics, it is confirmed that there is no moisture absorption in the sample formed at 1 Torr if the film is flat. Moreover, the film is deposited onto the lines and space with no gap. Thus, it could be considered that even if the super-fine particle silicon oxide film is actually mounted in an LSI, any problem of the moisture absorption is not brought about.

Figure 12:
FIG. 12 is a diagram indicating a photograph by the electron microscope which shows a result of deposition of the porous semiconductor oxide film onto lines with a 0.5 μm pitch.

FIG. 12 shows a sectional SEM image after the super-fine particle silicon oxide film was deposited on 0.5-µm lines and spaces at the condition of the 1 Torr ambient gas. The aspect ratio is 0.8. The space is filled with the film up to the bottom thereof, similarly to the case of 1-µm lines and spaces. However, a very small gap is confirmed at the center.

Figure 13:
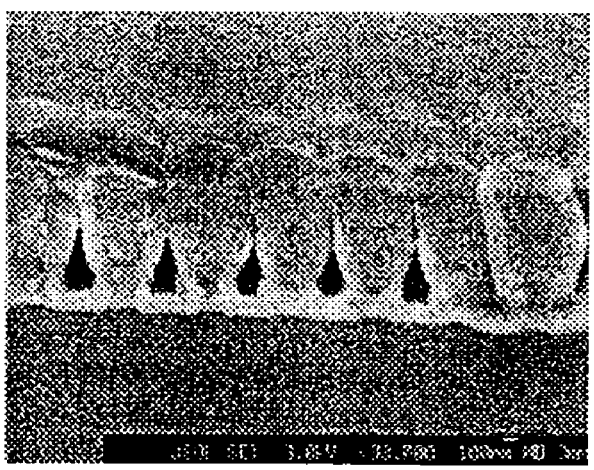
FIG. 13 is a diagram indicating a photograph by the electron microscope showing a result of deposition of the porous semiconductor oxide film onto a line with a 0.25 μm pitch.

FIG. 13 shows a sectional SEM image after the super-fine particle silicon oxide film was deposited on 0.25-µm lines and spaces at the condition of the 1 Torr ambient gas. The aspect ratio was 1.6. Although the super-fine particle film covered the resist pattern, the particle film did not fill the space between the lines. It is confirmed that the particle film expands on the resist in a horizontal direction associated with the growth of the film such that a particle is contacted with adjacent particles on the resist and further grown in an upper direction. As a result, the gap remains in the space.

In the gas evaporation method, while the vapor particle is collided with molecules of the ambient gas, the particles grow. Thus, the directionality in the deposition of the particles is low. Accordingly, the particle film is deposited on the resists, in the order starting from the resists located closer to the vaporization source. Therefore, it is considered that the particle film cannot fill in the case of 0.25 µm.

The super-fine particles formed by the mix-gas evaporation method in which 1-% $O_2$ and 99-% Ar are mixed are sufficiently oxidized. Although this is represented as $SiO_x$ (1<x<2), it is said that $SiO_2$ is dominant in the film. The particles do not have the form of a ball at any pressure. The particles are coupled to each other, and spread out in the form of a chain or a network. Moreover, the existence of the gap surrounded with the particles is confirmed by TEM. The particles are largely grown in the case produced under a higher pressure, similarly to the gas evaporation method performed using a rare gas.

From the result of the measurement of the capacitance, it is confirmed that the dielectric constant of the super-fine particle $SiO_x$ film is very small in any formation condition. As for the influence of the formation condition to the dielectric constant, there is a tendency that the dielectric constant becomes smaller as the gas pressure is increased higher. This reason may be considered as following. That is, if the ratios of the constituent elements are constant in any formation pressure, that is, if the degree of the oxidation is constant, the ratio of a portion occupied by the ambient gas between the particles to the whole film may be higher in the super-fine particle film formed under the higher pressure. The relative dielectric constant of 1.68 is recorded in the case formed at 10 Torr.

However, the moisture absorption is confirmed in the particle film formed at the high pressure. It is considered that the ratio of the portion occupied by the ambient gas is too large. This influence appears as the increase of the dielectric constant. The sample having the lowest dielectric constant among the samples with no moisture absorption is the sample formed at 1 Torr. Its relative dielectric constant is "1.83". This is superior in insulation property. The leak current is 1 nA or less when a voltage of 20 V is applied to the device in which the parallel flat plate electrodes with the area of 0.03 cm$^2$ are generated in the super-fine particle film with a film thickness of 500 nm. It is said that this value sufficiently satisfies the requirement as the interlayer insulating film.

The deterioration of the insulation and the increase of the dielectric constant due to the moisture absorption are not confirmed even after the sample is left in the atmosphere. The reasons why the moisture absorption does not occur irrespective of the porous film are considered as follows:

(a) the moisture cannot enter into the holes because the holes are extremely narrow; and (b) the holes are not consecutive and divided sporadically and thereby the moisture is absorbed only in the vicinity of the surface and can not invade up to the innermost.

In the evaluation of the coverage property, the sample formed at 10 Torr cannot fill the 1-μm space between lines having the aspect ratio of 0.4. However, the sample formed at 1 Torr can fill perfectly. This can be explained from the feature of the gas evaporation method. That is, as the gas pressure becomes higher, the directionalities of the formed particles become lower. This results in the increase of the rate of capture of the particles on the resist line located closer to the vaporization source. Even the sample formed at 1 Torr cannot fill the space of 0.25-μm between lines (aspect ratio of 1.6). Thus, the large gap is left. However, it is considered that since there is no gap at the upper portion of the silicon oxide film, the coverage is successfully performed.

Next, the semiconductor device of the present invention is made in accordance with the above mentioned results. The method of manufacturing it will be described below.

At first, a semiconductor circuit components are formed on a semiconductor substrate 1, as shown in FIG. 1A. Each of the semiconductor circuit components is provided with source drain regions 2 formed on a surface region of the semiconductor substrate 1, and a gate electrode 4 formed on the surface of the substrate 1 through a gate oxide film 3.

Figure 1B:
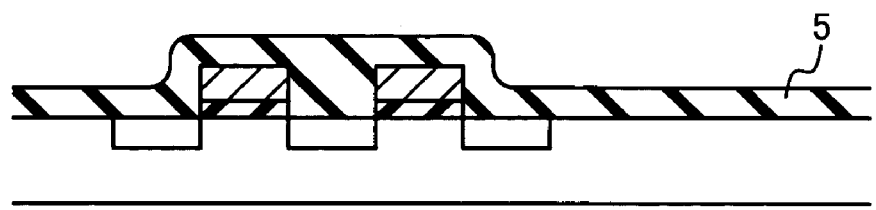

Next, the porous silicon oxide film is formed similarly to the above mentioned method, as shown in FIG. 1B.

The semiconductor substrate 1 on which the circuit components are formed, is positioned on the upper portion within the chamber 21. In the chamber 21, the silicon is used for the vapor source 23, and the BN (boron nitride) boat is used for the crucible 22a. By the supply of the electric power to the BN port 22, the silicon is heated and vaporized. The mixture gas of O$_2$ of 1% and Ar of 99% is used for the ambient gas in order to form the oxidized super-fine particles. The pressure of the ambient gas is in a range 0.3 Torr to 10 Torr. More preferably, the pressure of the ambient gas is in a range 0.5 Torr to 10 Torr. The vaporized silicon particles are collided against the ambient gas to be grown. At the same time, the silicon particles are oxidized by O$_2$ and deposited on the substrate placed 5 cm apart from the vaporization source as a porous super-fine particle silicon oxide film. The pressure of the ambient gas is a predetermined value from 0.5 Torr to 10 Torr. The growth time is 10 minutes.

Figure 1C:
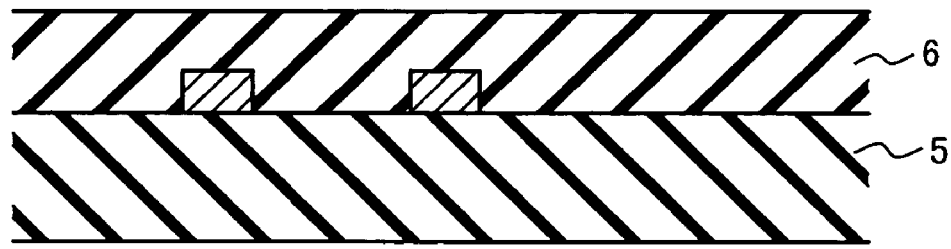
FIGS. 1C and 1D are cross sectional views explaining that the method of manufacturing the semiconductor device of the present invention can be applied to an insulation of a wiring pattern instead of FIG. 1A.
Figure 1D:
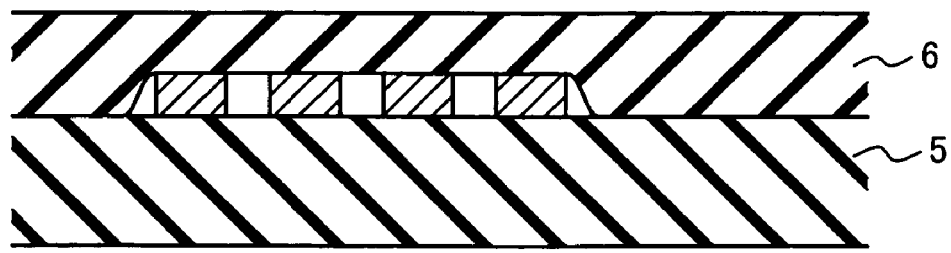

In the above mentioned explanation, the porous silicon (semiconductor) oxide film 5 is formed on the semiconductor circuit components. However, it may be formed on wiring patterns formed on another interlayer insulating film, as shown in FIG. 1C. The other interlayer insulating film may be porous semiconductor oxide film 5. Also, when the interval between the patterns is equal to or less than 0.25 μm, the method described below may be considered, as shown in FIG. 1D. That is, after the porous semiconductor oxide film 5 is formed, it is flattened by CMP. Then, another porous semiconductor oxide film 6 is deposited. In this case, the air is used for the insulation in the horizontal direction of the wiring pattern, and the porous semiconductor oxide film 6 is used for the insulation in the vertical direction. If this method is possible, the effective dielectric constant is considered to be further reduced. The lower interlayer insulating film may be a usual interlayer insulating film.

In the above-mentioned example, the pressure of the mixture gas is constant during the formation of the porous silicon oxide film. However, the pressure of the mixture gas may be changed during the formation of the porous silicon oxide film. That is, the pressure of the mixture gas is set first to 0.5 Torr, and then set to 1.0 Torr. Further, the pressure of the mixture gas may be set to 10 Torr, and finally set to 0.5 Torr. In this case, the dielectric constant can be decreased while the coverage property is improved.

Also, the pressure of the mixture gas is set first to 10 Torr, and then set to 0.5 Torr. In this case, the dielectric constant can be decreased using the air portion while the moisture absorption can be prevented.

As mentioned above, the present invention can provide the semiconductor device having the interlayer insulating film with the small dielectric constant, the adaptation to the wiring pattern material, the heat-proof property and the adaptation to the process, and the method of manufacturing the semiconductor device.

What is claimed is:

1. A method of manufacturing a semiconductor device, comprising:

forming semiconductor circuit elements or wiring patterns on a semiconductor substrate; and forming a porous silicon oxide film as an interlayer insulating film on said semiconductor substrate including said semiconductor circuit elements or wiring patterns by oxidizing silicon in a mixture gas containing an oxygen gas in a chamber, wherein the forming of the porous semiconductor oxide film includes supplying said mixture gas containing said oxygen into the chamber and vaporizing the silicon in the chamber, said mixture gas being at a pressure which is changed while said mixture gas is supplied, wherein said pressure of said mixture gas is set to a first pressure value in a range of 0.3 Torr to 10 Torr and then to a second pressure value in a range of 0.3 Torr to 10 Torr, the second pressure value being greater than the first pressure value.

2. A method according to claim 1, wherein said first and second pressure values of said mixture gas in the chamber are in a range of 0.5 Torr to 10 Torr.

3. A method according to claim 1, wherein said pressure of said mixture gas is set to a third pressure value in the range 0.3 Torr to 10 Torr, wherein the third pressure value is less than the second pressure value.

4. A method according to claim 1, wherein said step of supplying said mixture gas includes supplying said mixture gas containing said oxygen gas into the chamber such that said porous silicon oxide film covers said semiconductor circuit elements or wiring patterns while filling between said semiconductor circuit elements or wiring patterns.

5. A method according to claim 4, wherein an aspect ratio of a space between said semiconductor circuit elements or wiring patterns is equal to or smaller than 1.6.

6. A method according to claim 5, wherein an aspect ratio of a space between said semiconductor circuit elements or wiring patterns is equal to or smaller than 0.8.

7. A method according to claim 1, wherein said step of supplying said mixture gas includes supplying said mixture gas containing said oxygen gas into the chamber such that said porous silicon oxide film covers said semiconductor circuit elements or wiring patterns while forming gaps on side walls of said semiconductor circuit elements or wiring patterns.

8. A method according to claim 1, wherein said mixture gas contains said oxygen gas substantially equal to 1%.

9. A method according to claim 1, wherein said mixture gas includes an inert gas and said oxygen gas.

10. A method according to claim 1, wherein said porous semiconductor oxide film includes holes of an average diameter equal to or less than 20 nm.

11. A method according to claim 1, wherein said porous silicon oxide film includes $SiO_2$ equal to or more than 85%.

12. A method according to claim 1, wherein said step of forming a porous semiconductor oxide film includes forming said porous silicon oxide film to have a relative dielectric constant equal to or smaller than 1.95.

* * * * *

UNITED STATES PATENT AND TRADEMARK OFFICE
CERTIFICATE OF CORRECTION

PATENT NO. : 7,265,064 B2 Page 1 of 1
APPLICATION NO. : 10/938107
DATED : September 4, 2007
INVENTOR(S) : H. Morisaki et al.

It is certified that error appears in the above-identified patent and that said Letters Patent is hereby corrected as shown below:

| COLUMN | LINE | ERROR |
|---|---|---|
| On the title page item (56) col. 1, line 2, | Refs. Cited (U.S. Pats., | "Havemmann et al." should read --Havemann et al.-- |
| On the title page item (56) col. 2, line 1, | Refs. Cited (U.S. Pats., | "Havemmann et al." should read --Havemann et al.-- |
| On the title page item (57) col. 2, line 3, | Abstract 3 of text | "substrate then," should read --substrate. Then,-- |

Signed and Sealed this

Twenty Second Day of April, 2008

JON W. DUDAS
*Director of the United States Patent and Trademark Office*